United States Patent [19]

Hayakawa et al.

[11] Patent Number: 4,765,880

[45] Date of Patent: Aug. 23, 1988

[54] AIR/FUEL RATIO SENSOR

[75] Inventors: Nobuhiro Hayakawa; Shigeru Miyata; Tetsusho Yamada; Kazunori Yokota, all of Aichi, Japan

[73] Assignee: NGK Spark Plug Co., Ltd., Aichi, Japan

[21] Appl. No.: 912,462

[22] Filed: Sep. 29, 1986

[30] Foreign Application Priority Data

Sep. 27, 1985 [JP] Japan .................................. 60-214004
Feb. 17, 1986 [JP] Japan .................................. 61-32496

[51] Int. Cl.⁴ ............................................ G01N 27/46
[52] U.S. Cl. .................................... 204/425; 204/426
[58] Field of Search ....................... 204/1 S, 421–429

[56] References Cited

U.S. PATENT DOCUMENTS

| | | | |
|---|---|---|---|
| 3,691,023 | 9/1972 | Ruka et al. | 204/1 S |
| 3,700,577 | 10/1972 | Grauer | 204/420 |
| 4,207,159 | 6/1980 | Kimura et al. | 204/426 |
| 4,450,065 | 5/1984 | Yamada et al. | 204/426 |
| 4,496,455 | 1/1985 | Linder et al. | 204/425 |
| 4,502,939 | 3/1985 | Holfelder et al. | 204/427 |
| 4,574,627 | 3/1986 | Sakurai et al. | 204/426 |

*Primary Examiner*—T. Tung
*Attorney, Agent, or Firm*—Sughrue, Mion, Zinn, Macpeak & Seas

[57] ABSTRACT

An air/fuel ratio sensor having an unambiguous output with respect to both the fuel-rich and the fuel-lean regions and which does not require the introduction of atmospheric air. The sensor is composed of first and second elements, each having porous electrodes formed on opposite sides of an oxygen-ion-conductive electrolyte plate. The two elements are arranged to define between them a gas compartment communicating with the atmosphere to be detected via one or more diffusion limiting portions. One of the elements serves as an oxygen concentration differential electrochemical cell and the other one as an oxygen pump. An internal reference oxygen source is formed on the side of one of the elements opposite the gas compartment, and a small current is caused to flow the first element so as to transfer oxygens from the gas compartment to the oxygen source. The second element pumps oxygen into or out of the gas compartment in such a manner that the air/fuel ratio of the gas in the gas compartment is held at a predetermined value.

16 Claims, 5 Drawing Sheets

AIR/FUEL RATIO SENSOR

BACKGROUND OF THE INVENTION

The present invention relates to an A/F (air/fuel) ratio sensor used to detect the A/F ratio of the intake air/fuel mixture to an internal combustion engine or other combustor on the basis of the concentration of oxygen in the exhaust from the engine or combustor.

Various A/F ratio detectors have been used to detect the A/F ratio of the air-fuel mixture fed to an internal combustion engine or other combustor on the basis of the concentration of oxygen in the exhaust gas. One such device, as described in Unexamined Published Japanese Patent Application No. 178354/1984, includes two spaced elements, each having porous electrodes formed on opposite sides of a tubular oxygen-ion-conductive solid electrolyte. One of the elements is used as an oxygen pump for pumping oxygen out of the gap between the two elements, and the other element is used as an oxygen concentration electrochemical cell which produces a voltage in accordance with the difference in oxygen concentration between the gap and the ambient atmosphere. This device is capable of detecting the A/F ratio in the fuel-lean region of the intake mixture.

However, this type of A/F ratio sensor, which is principally designed for use only in the fuel-lean region where the exhaust gas contains a large amount of residual oxygen, produces a similar signal in the fuel-rich region where the exhaust gas contains a very small amount of residual oxygen due to the presence of oxygen-containing species in the exhaust gas such as CO, $CO_2$ and $H_2O$. In other words, each value of the output signal from the A/F ratio sensor (except for precisely at the stoichiometric value) can represent either one of two different values of A/F ratio; that is, the sensor output is ambiguous with respect to the fuel-lean and fuel-rich regions. Therefore, this A/F ratio sensor cannot be used for A/F ratio control unless it is known definitely whether the combustor is operating in the fuel-lean or fuel-rich region.

To overcome this problem, it has been proposed to introduce atmospheric air in contact with the side of the oxygen concentration electrochemical cell which does not face the oxygen pump, thereby preventing the detected signal from being inverted in the vicinity of the stoichiometric value of the A/F ratio. However, in order to introduce atmospheric air in contact with one side of the oxygen concentration electrochemical cell, the A/F ratio sensor must be open to the ambient atmosphere, but this in turn makes the sensor construction complex due to the difficulty in making it waterproof.

In order to eliminate this problem, two modifications have been proposed. According to the first modification, instead of introducing atmospheric air into the sensor, oxygen is generated by an internal reference oxygen source device incorporating an electrochemical oxygen pump cell and provided on one side of the oxygen concentration electrochemical cell, and part of the oxygen generated in the device is caused to leak into the ambient exhaust gas through a leakage resisting portion so that the oxygen partial pressure in the internal reference oxygen source is maintained constant. (See Japanese Patent Application No. 137586/1985). This approach obviates the need for an atmospheric reference. According to the second modification, the need for an atmospheric reference is eliminated by using a "current limiting" sensor in combination with a lambda sensor. (See SAE Technical Paper No. 850379).

The above-described A/F ratio sensor where part of the oxygen evolved at the internal reference oxygen source device is caused to leak into the ambient exhaust gas has the disadvantage that if the oxygen partial pressure in the ambient exhaust gas changes, a corresponding change occurs in the oxygen partial pressure within the internal reference oxygen source. This problem is particularly pronounced when the exhaust gas is in the fuel-rich state. This is because inflamable gas components such as CO and $H_2$ contained in an exhaust gas held in a fuel-rich condition will pass through the leakage resisting portion so that a great amount of the gas will be diffused reversely into the internal reference oxygen source. It is confirmed that the pressure of the oxygen in the source is largely reduced to generate a significant error in the output of the oxygen concentration electrochemical cell. A further problem of this sensor arises from the fact that the opening at the leakage resisting portion of the internal reference oxygen source is exposed to the exhaust gas. As a result, deposits of certain glass-forming components of the exhaust gas can form at the opening of the leakage resisting portion, leading to substantial blocking of the internal reference oxygen source and causing an abnormal increase in the internal oxygen partial pressure, which renders correct detection of the A/F ratio impossible or may even lead to complete failure of the sensor.

SUMMARY OF THE INVENTION

Overcoming the above-discussed drawbacks, the A/F ratio sensor of the present invention avoids introducing atmospheric air in contact with one side of the oxygen concentration electrochemical cell but still attains the same effect as obtained by such introduction of atmospheric air. The inventive A/F ratio sensor is characterized by comprising:

a first element A having a pair of porous electrodes 1 and 2 on opposite sides of an oxygen-ion-conductive solid electrolyte plate 3;

a second element B having a pair of porous electrodes 4 and 5 on opposite sides of an oxygen-ion-conductive solid electrolyte plate 6;

a gas compartment in contact with both the porous electrode 2 of the first element and the porous electrode 4 on the second element and which communicates with the gaseous atmosphere of interest by way of a gas diffusion limiting portion; and an internal reference oxygen source in contact with the porous electrode 1 of the first element and which communicates with the gas compartment by way of a leakage resisting portion.

A typical example of the oxygen-ion-conductive solid electrolyte used in the first and second elements is a solid solution of zirconia and yttria or calcia. Other usable materials include solid solutions of cerium dioxide, thorium dioxide and hafnium dioxide; a solid solution of the perovskite type oxide; and a solid solution of a trivalent metal oxide. The porous electrodes 1, 2, 3 and 4 formed on the opposite sides of the solid electrolytes may be formed of platinum, rhodium or other metal which catalyzes an oxydative reaction. The electrodes may be formed by various methods. In one method, a paste based on a powder of platinum, gold or any other appropriate metal and which is mixed with a powder of the same ceramic material as the solid electrolyte is printed in a predetermined pattern on the solid electrolyte by a thick-film deposition technique and the printed coat is sintered. In another method, the powder of the starting material is applied onto the solid electrolyte by a suitable thin-film deposition technique such as flame spraying, chemical plating or evaporation. The porous electrodes 2, 3 and 4 which are to be exposed to the exhaust gas are preferably coated with a porous protective layer of alumina, spinel, zirconia, mullite or the like formed by a thick-film deposition technique.

The gas compartment is a space into which the ambient exhaust gas is introduced in a diffusion-limiting manner through a gas diffusion limiting portion. This compartment may be formed by inserting a spacer, namely, a laminar intermediate member made of $Al_2O_3$, spinel, forsterite, steatite, zirconia or the like, between the first and second elements such that a flat closed compartment is defined between the porous electrode 2 on the first element and the porous electrode 3 on the second element. The spacer is provided with apertures that serve as a gas diffusion limiting portion and which establish communication between the ambient gaseous atmosphere and the gas compartment. The gas diffusion limiting portion is not limited to any particular shape so long as it is capable of establishing communication between the ambient gaseous atmosphere and the gas compartment in a diffusion limiting manner or a like manner. For example, the spacer may be partly or entirely replaced by a porous body or, alternatively, apertures may be provided in the spacer (the spacer may form a coated thick film). If desired, the spacer may be provided only in the area between the terminal side of the first elements and that of the second element, thereby forming a gap between the first and second elements which serves as a gas diffusion limiting gap and also as the gas compartment. The gas compartment may be entirely filled with a porous material, which is desirably an electrical insulator.

If the gas compartment is in a flat form as described above, its thickness (the distance between the surfaces of the porous electrodes on the two elements) is preferably within the range of 0.01 to 0.2 mm, with the range of 0.05 to 0.1 mm being particularly preferable. If the thickness of the gas compartment is smaller than 0.1 mm, the diffusion of oxygen gas is limited to such a great extent that the responsiveness of the A/F ratio sensor is decreased rather than increased. In addition, if the thickness of the gas compartment is too small, it has a tendency to deform during the fabrication of the sensor and will not then provide reliable electrical insulation, with the result that sensors of consistent quality are difficult to obtain. If, on the other hand, the thickness of the gas compartment is greater than 0.2 mm, the difference in partial pressure of constituent gases that develops across the thickness of the gas compartment is increased, which causes not only an undesirable increase in the pump current, but also reduced sensor responsiveness.

The internal reference oxygen source serves as a collector of oxygen which is extracted from the gas compartment by means of the current flowing through the first element. The oxygen source may be formed by the combination of a shield plate, which may be made of $Al_2O_3$, spinel, forsterite, steatite, zirconia or the like and which has a recess matching the shape of the porous electrode 1 on the first element on which the shield is placed, and a layer of porous material as a leakage resisting portion, one side of which is exposed to the inner surface of the recess and the other side of which is exposed to the gas compartment by way of a through-hole in the first element. The leakage resisting portion has a high resistance to gas diffusion (small gaseous conductance) and serves to cause gradual movement of oxygen from the internal reference oxygen source into the gas compartment. The porous layer may be replaced by tiny holes which penetrate the first element and reach the interior of the gas compartment. The internal reference oxygen source may be formed using the communicating pores in the porous electrode 1 instead of providing a recess in the shield plate.

The first element operates as an oxygen generator and coincidently as an oxygen concentration electrochemical cell, while the second element serves as an oxygen pump.

One of the functions to be fulfilled by the first element is to generate oxygen. This is accomplished by the ability of the solid electrolyte to permit the movement of oxygen ions through a plate of the solid electrolyte when a voltage is applied between the electrodes on the opposite sides of the plate under appropriate temperature conditions ($\geq 400°$ C. if the solid electrolyte is made of stabilized zirconia). When a voltage is applied between the porous electrode 2 in contact with the gas compartment and the porous electrode 1 in contact with the internal reference oxygen source in such a manner that oxygen ions flow from the porous electrode 2 toward the porous electrode 1 (i.e., the porous electrode 2 is negatively biased while the porous electrode 1 is positive), oxygen is transported from the gas compartment to the vicinity of the porous electrode 1, thereby evolving oxygen within the internal reference oxygen source.

The first element also functions as an oxygen concentration electrochemical cell which utilizes the ability of the solid electrolyte plate to develop a voltage (electromotive force) corresponding to the differential oxygen partial pressure between opposite sides of the plate when it is exposed to appropriate temperature conditions. The first element measures the oxygen partial pressure within the gas compartment as against the oxygen in the internal reference oxygen source.

The second element is an oxygen pump having the same operating principle as that for the first element when it acts as an oxygen generator: oxygen ions move through the solid electrolyte plate when a voltage is applied between opposite sides of the plate under appropriate temperature conditions. Upon application of a voltage between the two porous electrodes 4 and 5, the oxygen pump element pumps oxygen out of or into the gas diffusing compartment.

The basic operation of the A/F ratio sensor of the present invention will now be described.

First, a predetermined amount of current is caused to flow by applying a predetermined voltage (for example, 5 volts) through a resistance (for example, 500 kilo-ohms) between the porous electrodes 1 and 2 of the first element in such a manner that the electrode 1 is positively biased while the electrode 2 is negative. As a result, oxygen is transported from the gas compartment to the internal reference oxygen source.

When the oxygen partial pressure at the internal reference oxygen source becomes higher than the oxygen partial pressure in the gas compartment, an electromotive force which is proportional to the differential oxygen partial pressure is developed between the porous electrodes 1 and 2. The resulting terminal voltage varies by as much as several hundred millivolts between the case where the gas in the gas compartment is fuel-rich and the case where it is fuel-lean. This difference is sufficiently great to cause an abrupt change in the sensor output at the stoichiometric value of the A/F ratio (the point where the fuel-rich region meets the fuel-lean region).

Making use of these characteristics of the first element, the second element pumps oxygen into or out of the gas compartment in such a manner that the A/F ratio of the gas in the gas compartment is held substantially at the stoichiometric value ($\lambda=1$), irrespective of the A/F ratio of the ambient exhaust gas.

More preferably, the second element is actuated to pump oxygen out of or into the gas compartment in such a manner that the voltage between the terminals at the first element is held at a predetermined value. The current which flows through the second element (hereunder referred to as the pump current) is detected as an output indicative of the A/F ratio of the exhaust gas. Alternatively, the pump current flowing through the second element may be controlled to be held at a predetermined constant value, and the resulting voltage which is developed between the terminals of the first element is detected as a signal indicative of the A/F ratio of the exhaust gas. Whichever method is used, highly precise measurement is realized since the oxygen partial pressure at the internal reference oxygen source is maintained at a constant level.

Further, the operating mechanism of the A/F ratio sensor of the present invention will be described for the case where the pump current flowing through the second element is adjusted such that the terminal voltage across the first element is held constant.

It is assumed that steady-state conditions are present whereby the A/F ratio of the gas in the gas compartment is maintained at the stoichiometric value ($\lambda=1$) by the action of the first and second elements. The amount of oxygen which moves from the gas compartment into the internal reference oxygen source through the solid electrolyte plate is expressed by the following equation (which contains the diffusion coefficient D as a parameter):

$$(RT/4F)I_{cp} = C \cdot D_{O2}(PS_{O2} - PO_{O2}) + \qquad (1)$$
$$C \cdot D_{H2}(PO_{H2} - PS_{H2})/2 +$$
$$C \cdot D_{CO}(PO_{CO} - PS_{CO})/2$$

where
R: gas constant (N·m·K$^{-1}$·mol$^{-1}$)
T: absolute temperature (K)
F: Faraday constant (coulomb·mol$^{-1}$)
$I_{cp}$: current (coulomb·sec$^{-1}$)
C: leakage conductance (m)
$D_{O2}$: diffusion coefficient of $O_2$ (m$^2$·sec$^{-1}$)
$D_{H2}$: diffusion coefficient of $H_2$ (m$^2$·sec$^{-1}$)
$D_{CO}$: diffusion coefficient of CO (m$^2$·sec$^{-1}$)
$PS_{O2}$: pressure of $O_2$ in the internal reference oxygen source (N·m$^{-2}$)
$PS_{H2}$: pressure of $H_2$ in the internal reference oxygen source (N·m$^2$)
$PS_{CO}$: pressure of CO in the internal reference oxygen source (N·m$^{-2}$)
$PO_{O2}$: pressure of $O_2$ in the gas compartment (N·m$^{-2}$)
$PO_{H2}$: pressure of $H_2$ in the gas compartment (N·m$^{-2}$)
$PO_{CO}$: pressure of CO in the gas compartment (N·m$^{-2}$).

The left side of equation (1) represents the rate of oxygen flow through the solid electrolyte. The first term on the right side represents the rate of oxygen flow from the internal reference oxygen source into the gas compartment through the leakage resisting portion. The second and third terms on the right side represent the rates of oxygen flow in the internal reference oxygen source, which flows are respectively consumed by $H_2$ and CO moving from the gas compartment into the internal reference oxygen source through the leakage resisting portion. The symbol C on the right side of equation (1) signifies the conductance of a gas passing through the leakage resisting portion; the greater the value of C, the greater the gas leakage.

In the internal reference oxygen source where oxygen is stored, it may generally be assumed that $PS_{H2}=0$ and $PS_{CO}=0$. Hence, equation (1) can be rewritten as:

$$PS_{O2} = (1/CD_{O2}) \cdot (RT/4F) \cdot I_{cp} - \qquad (2)$$
$$(1/D_{O2}) \cdot (D_{H2}PO_{H2} + D_{CO}PO_{CO}) + PO_{O2}$$

Therefore, $PS_{O2}$ depends on $PO_{O2}$, $PO_{H2}$ and $PO_{CO}$. However, since the A/F ratio of the gas in the gas compartment is controlled to be substantially at $\lambda=1$, $PO_{O2}$, $PO_{H2}$ and $PO_{CO}$ are constant, and thus $PS_{O2}$ (the oxygen partial pressure in the internal reference oxygen source) is also constant.

DESCRIPTION OF THE PREFERRED EMBODIMENTS

A first preferred embodiment of an A/F ratio sensor of the present invention will hereunder be described with reference to FIG. 1, which is a partial fragmentary perspective view of the sensor, and to FIG. 2A, which shows the sensor of FIG. 1 in a disassembled state. For the sake of clarity, the various parts in each figure are not drawn to scale.

Figure 1:
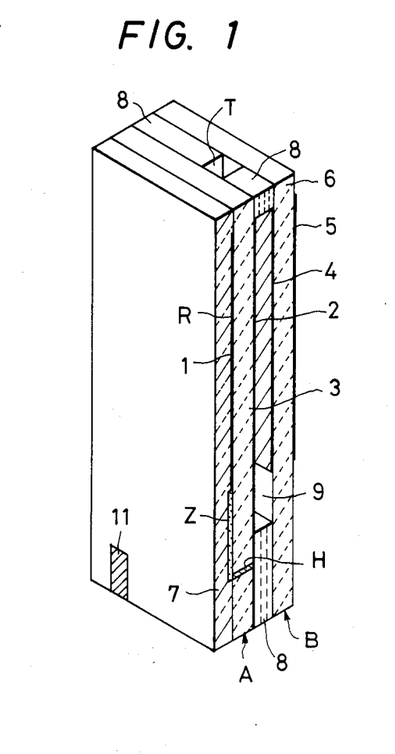
FIG. 1 is a partially fragmentary perspective view illustrating an A/F ratio sensor of a first embodiment of the present invention.
Figure 2A:
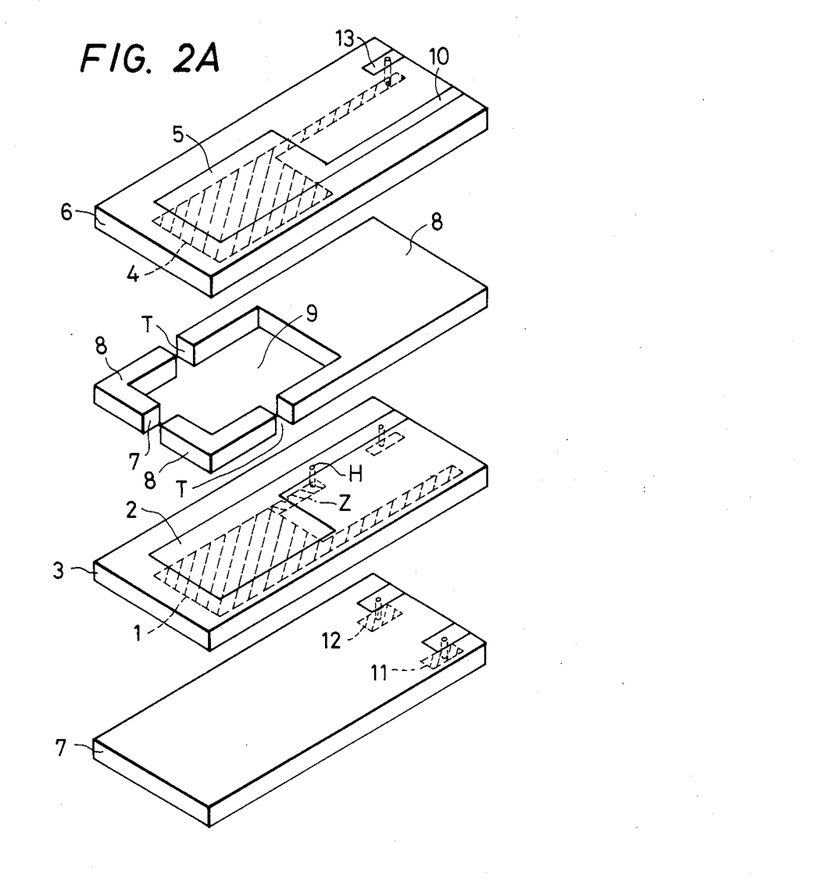
FIG. 2A is a perspective view showing the sensor of FIG. 1 in a disassembled state.

As illustrated in FIGS. 1 and 2A, the A/F ratio sensor of the first embodiment of the present invention includes:

a first element A having porous electrodes 1 and 2 formed on opposite sides of a solid electrolyte plate 3;

a second element B having porous electrodes 4 and 5 formed on opposite sides of a solid electrolyte plate 6;

an internal reference oxygen source R formed by the porous electrode 1 at the interface between the first element A and a shield plate 7, the porous electrode 1 being buried in the solid electrolyte plate 3 in the embodiment under discussion;

a leakage resistance portion defined by a porous insulator Z, a through-hole H, and a porous lead to the porous electrode 2, one end of the porous insulator Z being in contact with the porous electrode 1 and the other end in contact with the lead of the porous electrode 2 via the through-hole H; and a gas compartment 9 formed between the porous electrode 2 and 4 on the first and second elements A and B, respectively, which are stacked together with a spacer 8 inserted therebetween as a laminar intermediate member. In the embodiment shown, the spacer 8 is cut out at three points to provide apertures serving as gas diffusion limiting portions T.

The porous electrode 5 is connected to a terminal 10, while the porous electrode 1, 2 and 4 are connected to terminals 11, 12 and 13, respectively, through associated communicating holes.

Figure 2B:
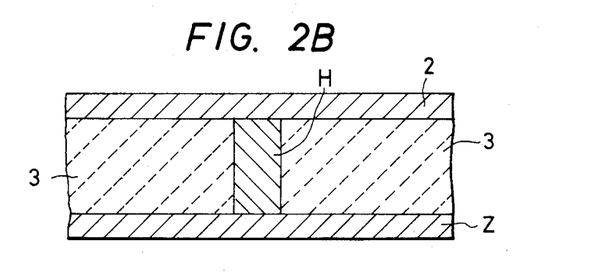
FIG. 2B is a partial cross section showing a through-hole H in the sensor of FIG. 1.

The through-hole H, which is one element of the leakage resisting portion, may have the structure shown in FIG. 2B, which is a partial sectional view of the hole. As shown in FIG. 2B, the through-hole H is filled with a porous material of the same type as the material of the porous electrode 2. It should, however, be noted that the through-hole H may be filled with the porous insulator Z or it may be left unfilled. The only requirement for the structure of the through-hole H is that it allow oxygen to leak from the porous insulator Z to the porous electrode 2.

The dimensions of the individual components of the sensor of this embodiment are as follows: Each of the solid electrolyte plates 3 and 6 measures 0.5 mm thick, 4 mm wide and 25 mm long. Each of the porous electrodes 1, 2, 4 and 5 measures 2.4 mm by 7.2 mm. The spacer 8 measures 60 microns thick, 4 mm wide and 25 mm long. The gas compartment 9 formed in the spacer 8 measures 2.4 mm by 7.7 mm, and the gas diffusion limiting portions T are in the form of three apertures each 0.5 mm wide. The shield plate 7 measures 0.5 mm thick, 4 mm wide and 25 mm long. The porous insulator Z is made of $Al_2O_3$ and measures 1 mm wide, 10 mm long and 30 microns thick. The through-hole H has a diameter of 0.7 mm.

The solid electrolyte plates 3 and 6 serving as the bases for the first and second elements A and B, respectively, are formed of a $Y_2O_3$—$ZrO_2$ based solid electrolyte. Each of the electrodes 1, 2, 4 and 5 is formed of a porous body wherein platinum is doped with 10 wt% of $Y_2O_3$—$ZrO_2$. Both the shield plate 7 and the spacer 8 are made of zirconia.

Figure 3:
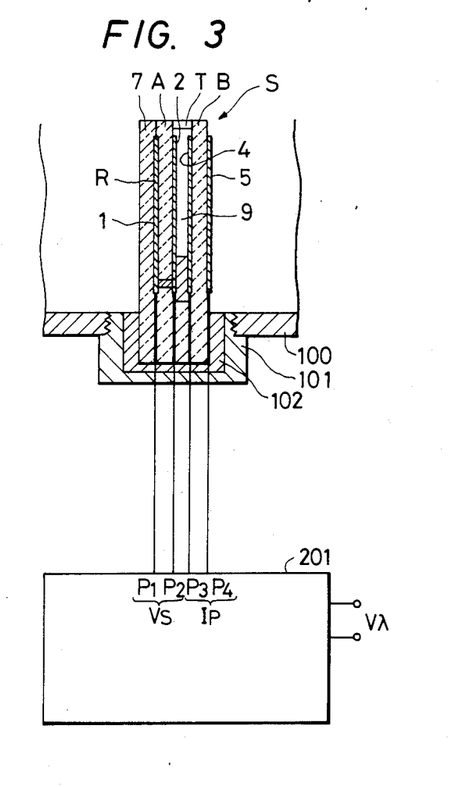
FIG. 3 is a diagram illustrating an application of the sensor of FIG. 1.

An example of the operation of the sensor of the first embodiment will hereunder be described with reference to the diagram shown in FIG. 3. For the sake of clarity, the sensor S in FIG. 3 is shown with the terminals 10, 11, 12 and 13 omitted, and with the porous electrodes 1, 2, 4 and 5 being directly connected to lead wires from an associated circuit.

The A/F ratio sensor S is attached to an exhaust pipe 100 by a threaded portion 101 and a fixing portion 102. The lower end of the sensor S is airtightly closed with the fixing portion 102 so that oxygen cannot leak out of the internal reference oxygen source and escape to the ambient atmosphere through the lead to the porous electrode 1.

The porous electrodes 1 and 2 of the first element A and the electrodes 4 and 5 of the second element B are connected to an A/F ratio signal detector circuit 201.

The detector circuit 201 causes a predetermined small current to flow through the first element A so as to produce a given oxygen partial pressure in the internal reference oxygen source R formed in the area of the porous electrode 1. At the same time, the detector 201 effects bidirectional control of the pump current flowing through the second element B in such a manner that the output between the porous electrodes 1 and 2, which is proportional to the differential oxygen partial pressure between the reference oxygen source R and the gas compartment 9, is held at a predetermined constant voltage; that is, the A/F ratio of the gas in the gas diffusion compartment 9 is maintained at a constant level. The value of the current obtained as a result of this bidirectional control is detected as an A/F ratio signal $V_\lambda$.

Figure 4:
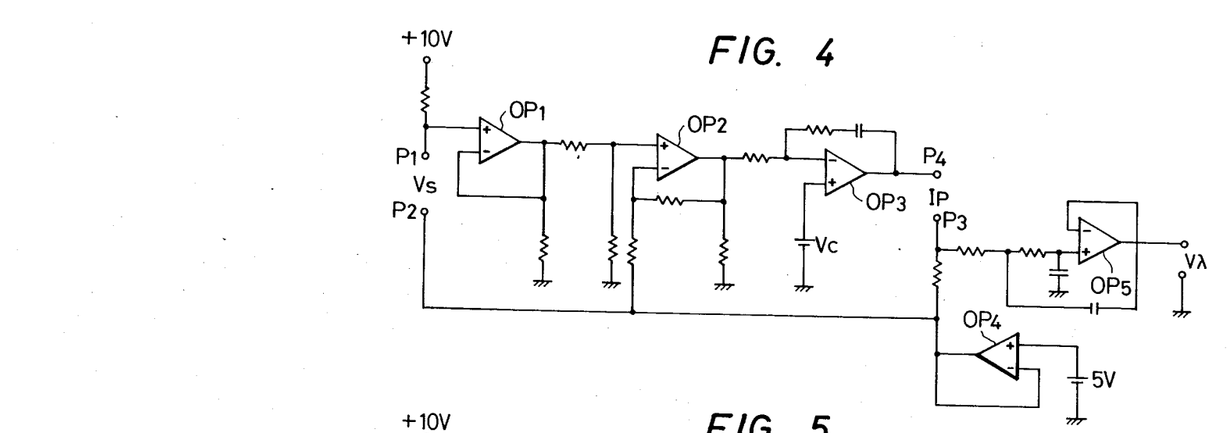
FIG. 4 is a circuit diagram of an A/F ratio signal detector which may be used to operate the sensor of FIG. 1.

The A/F ratio signal detector circuit 201 may be designed embodying five operational amplifiers OP1 to OP5 as shown in FIG. 4. An output $V_s$ from the first element A is amplified and compared with a reference voltage $V_c$. The differential voltage between the two is used to control the pump current in two directions for the purpose of maintaining $V_s$ at a constant level. The pump current so controlled is applied to OP5, which delivers an A/F ratio signal $V_\lambda$ as its output.

The A/F ratio sensor of this embodiment may effect measurement of the A/F ratio by employing a circuit which makes the potential of the porous electrode 2 equal to that of the electrode 4. In this case, contact between the porous electrodes 2 and 4 will not interfere with the measurement of the A/F ratio. Therefore, the two electrodes 2 and 4 may be formed as a unitary electrode by employing a circuit of the configuration shown in FIG. 5, wherein a terminal P11 is connected to the porous electrode 1, a terminal P12 to the electrodes 2 and 4 formed as a single integral electrode, and a terminal P14 to the porous electrode 5.

Figure 6:
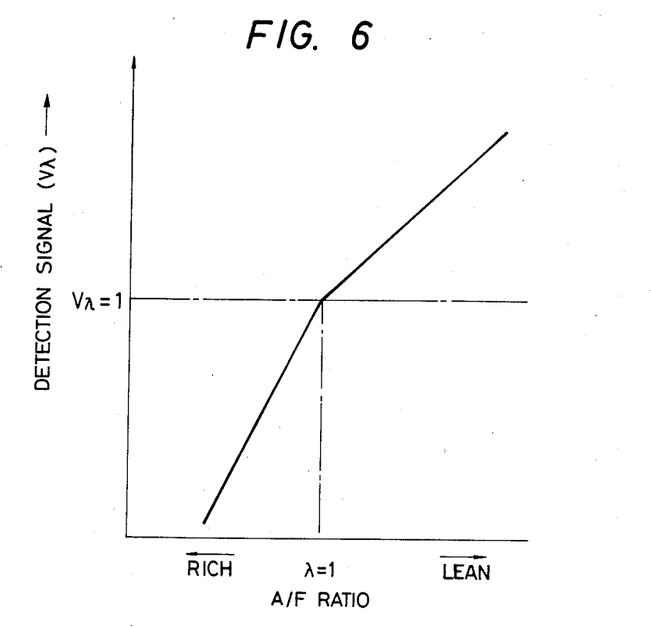
FIG. 6 is a characteristic diagram showing the A/F ratio vs. output signal from the sensor of FIG. 1 when connected to the detector circuit.

Using the A/F ratio signal detector circuit 201 described above, characteristics indicated by a solid line in FIG. 6 are obtained, wherein the A/F ratio signal $V_\lambda$ changes continuously from the fuel-rich to the fuel-lean region passing through the point corresponding to the reference voltage $V_\lambda 1$ =for $\lambda=1$.

The operating characteristics of the A/F ratio sensor of the first embodiment will hereunder be described in further detail.

Suppose first that the pump current flowing through the second element B is controlled such that the output voltage from the first element is held at a constant value in order to control the oxygen content of the gas compartment in such a manner that $\lambda$ is substantially unity. In this case, $PS_{O2}$ is much greater than $PO_{O2}$, $PO_{H2}$, $PO_{CO}$, $PS_{H2}$ and $PS_{CO}$, so that equation (1) can be rewritten as follows:

$$(RT/4F)I_{cp}=C \cdot D_{O2} \cdot PS_{O2} \tag{3}$$

Equation (3) indicates that $PS_{O2}$ is determined if both $I_{cp}$ and C or $C \cdot D_{O2}$ are known.

Therefore, to determine the leakage conductance C, the present inventors prepared four samples of an A/F ratio sensor in accordance with the first embodiment which had different values of resistance to gas leakage. Since it was impossible to determine the value of C directly, the inventors applied a voltage of zero volts to the porous electrode 1 on the first element and a voltage of 500 millivolts to the porous electrode 2 while ambient atmospheric air ($O_2$ partial pressure=0.2 kg/cm$^2$) was introduced into the air gas compartment 9 (the second element was not actuated). The values of $I_{cp}'$ (the current which flows from the porous electrode 1 into the electrode 2 when the four samples of the sensor were exposed to a temperature of 600° C.) were measured, and $I_{cp}'$ was used as an index for the leakage of gas. Therefore, if the applied voltage E (500 mV) and the oxygen partial pressure in the gas compartment $PO_2'$ (which is constant in the case under discussion since the gas compartment is filled with atmospheric air) are known, the oxygen partial pressure in the internal reference oxygen source is determined to be constant from the well-known Nernst equation:

$$E = (RT/4F) \cdot \log_e (PO_2'/PS_{O2}') \quad (4)$$

If $PO_2'$ and $PS_{O2}$ are known, the value of C (or $C \cdot D_{O2}$, which is proportional to $I_{cp}'$, the current flowing between the porous electrodes 1 and 2) can be determined from the following equation:

$$(RT/4F)I_{cp}' = C \cdot D_{O2}(PO_2' - PS_{O2}') \quad (5)$$

Figure 7:
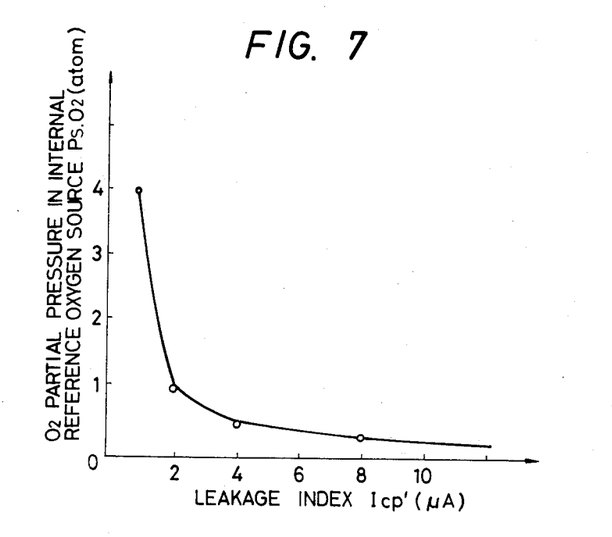
FIG. 7 is a diagram showing the leakage index vs. pressure of reference oxygen in the sensor of FIG. 1.

FIG. 7 shows the relationship between $I_{cp}'$ and $PS_{O2}$ (oxygen partial pressure in the internal reference oxygen source) for four samples of the A/F ratio sensor where the A/F ratio ( ) of the gas in the gas compartment was held at unity and an $I_{cp}$ of 10 microamps was caused to flow between the porous electrodes 1 and 2. The values of $PS_{O2}$ were calculated by substituting $CD_{O2}$ and $I_{cp}$ into equation (3), with the former being determined from $I_{cp}'$ by equation (5). The measured values are indicated in FIG. 7 by circles.

One can see from FIG. 7 that beyond a certain level of leakage resistance (for instance ≧4 microamps in terms of $I_{cp}'$), the change in $PS_{O2}$ (oxygen partial pressure in the internal reference oxygen source) is very small, negligible for practical purposes.

A second embodiment of an A/F ratio sensor of the present invention will hereunder be described with reference to FIG. 8, which shows a perspective view of the leakage resisting portion of the sensor.

The sensor of the second embodiment is identical to that of the first embodiment with respect to construction, material, fabrication process and method of use, except for the location of the leakage resisting portion in the first element A.

Figure 8:
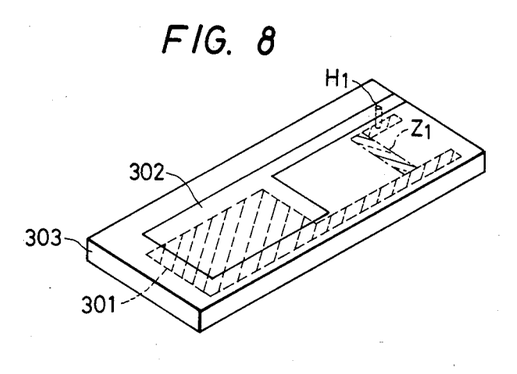
FIG. 8 is a perspective view illustrating the leakage resisting portion of a sensor constructed according to a second embodiment of the present invention.

The leakage resisting portion of the sensor shown in FIG. 8 is defined by a porous lead to an electrode 301, a porous lead to an electrode 302, a through-hole H1 connecting the terminal 12 to the lead to the electrode 302, and a porous insulator Z1 provided between the lead to the electrode 301 and the through-hole H1.

Figure 9A:
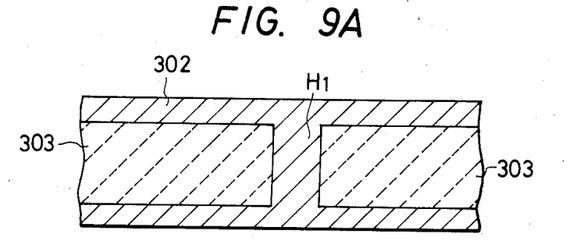
FIGS. 9A and 9B are partial cross sections showing two embodiments of a through-hole in the sensor of FIG. 8.

As shown in partial cross section in FIG. 9A, the through-hole H1 is filled with the same material as that of the porous electrode 302, and hence is not only porous but also conductive.

Figure 9B:
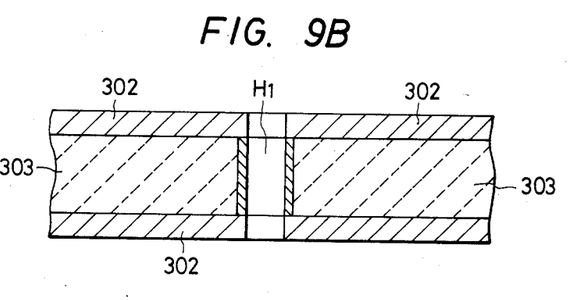

Another arrangement of the through-hole H1 is shown in cross section in FIG. 9B, wherein the hole is coated with a conductive material only on its inner surface.

Figure 5:
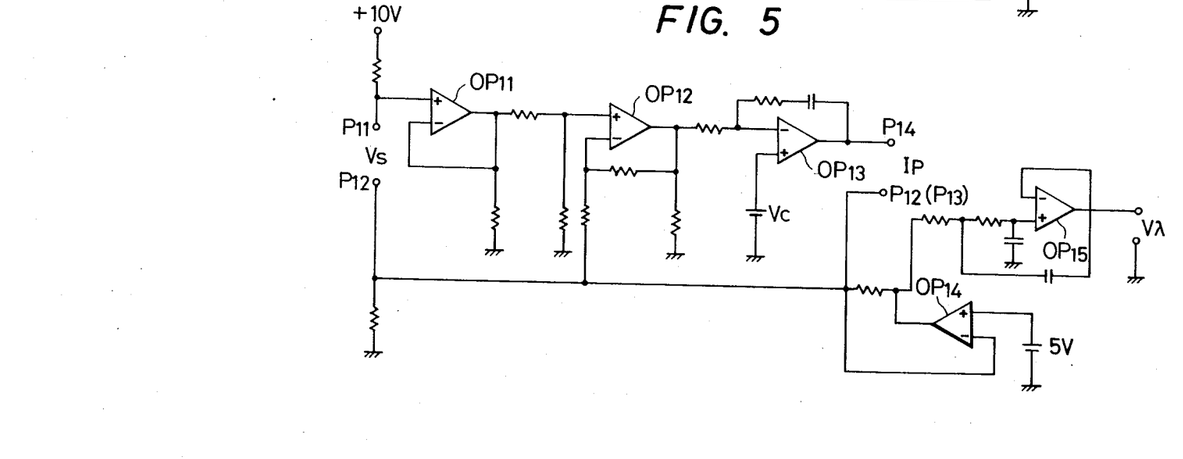
FIG. 5 is a circuit diagram of a modified version of the A/F ratio signal detector.

The A/F ratio sensor of the second embodiment may be operated with an A/F ratio signal detector circuit as shown in FIG. 4 or 5.

The leakage resisting portion of the sensor of the second embodiment is longer than its counterpart in the first embodiment. Thus, in addition to the advantages attained by the first embodiment, this leakage resisting portion affords a higher degree of resistance to gas leakage and lends itself to providing an even higher level of stability in the value of $PS_{O2}$, the oxygen partial pressure in the internal reference oxygen source. In addition, only one hole needs to be made in the solid electrolyte plate 303 since the through-hole extending to the lead to the porous electrode 302 also serves as the through-hole in the leakage resisting portion. This helps not only in maintaining the structural integrity of the solid electrolyte plate 303, but also in reducing the number of steps involved in sensor fabrication.

In the A/F ratio sensor of the present invention, a constant current is maintained flowing through the first element A so as to generate oxygen in the internal reference oxygen source, and the oxygen thus generated is caused to leak into the gas compartment, which is thus always filled with an atmosphere having a constant composition. As a result, the pressure of reference oxygen is stabilized and the A/F ratio of the feed gas to an automotive internal combustion engine or other combustor can be measured as precisely as when the atmospheric air is employed as a reference.

The A/F ratio sensor of the present invention thus does not have to be provided with an opening through which atmospheric air is introduced, and it can be easily rendered sufficiently waterproof.

In addition, because the leakage resisting portion in the sensor is not exposed to the ambient exhaust gas, the sensor can operate reliably for an extended period without allowing deposits from the exhaust gas to form in the leakage resisting portion. The sensor of the present invention has the additional advantage that variations in leakage resisting characteristics produced during fabrication can be reduced to a level that does not interfere with the measurement of the A/F ratio. Therefore, high-quality products having a consistent performance can be manufactured without the need for extra finishing steps such as trimming.

What is claimed is:

1. An air/fuel ratio sensor for sensing a gaseous atmosphere, comprising:
   a first element having first and second porous electrodes on opposite sides of an oxygen ion-conductive solid electrolyte plate;
   a second element having first and second porous electrodes on opposite sides of an oxygen ion-conductive solid electrolyte plate;
   means for defining a gas compartment disposed between said second electrode of the first element and said first electrode of the second element, said gas compartment defining means having a gas diffusion limiting portion through which said gas compartment communicates with the gaseous atmosphere;
   means for defining an internal reference oxygen source in contact with said first electrode of the first element;
   leakage resisting portion means for enabling gradual movement of oxygen from said internal reference oxygen source means to said gas compartment;

means for causing a predetermined amount of current to flow through the first element so that oxygen from the gas compartment is transferred to the internal reference oxygen source;

control means for controlling the current flow through the second element, the current flow being controlled to pump oxygen into or out of said gas compartment so that the voltage between the electrodes of the first element is held at a predetermined value; and means for measuring the air/fuel ratio of the gaseous atmosphere based on the current flow in said second element as a result of said control means.

2. The air/fuel ratio sensor of claim 1 wherein each of said first and second porous electrodes of the first element is provided with a porous lead portion, and wherein said leakage resisting portion means comprises a porous insulator extending from one of said first and second porous electrodes of the first element, and a through-hole formed between said porous insulator and said porous lead portion of the other of said first and second porous electrodes of the first element.

3. The air/fuel ratio sensor of claim 2, wherein said through hole is filled with a porous material.

4. The air/fuel ratio sensor of claim 3, wherein said porous material filling said through-hole is of the same material of which said porous electrodes of the first element are formed.

5. The air/fuel ratio sensor of claim 2, wherein said through-hole is unfilled.

6. The air/fuel ratio sensor of claim 1, wherein each of said first and second porous electrodes of said first element is provided with a porous lead portion, and wherein said leakage resisting portion means comprises a porous insulator extending from said porous lead portion of one of said first and second porous electrodes of said first element and substantially orthogonal thereto and connected to a terminal portion of the other one of said first and second porous electrodes, and a through-hole being formed between said terminal portion and said porous insulator.

7. The air/fuel ratio sensor of claim 6, wherein said through-hole is filled with a conductive porous material and serves to make part of external connection between said terminal portion and said porous insulator.

8. The air/fuel ratio sensor of claim 6, wherein said through-hole is lined with a conductive material and serves to make part of external electrical connection between said terminal portion and said porous insulator.

9. An air/fuel ratio sensor for sensing a gaseous atmosphere, comprising:

a first element having first and second porous electrodes on opposite sides of an oxygen ion-conductive solid electrolyte plate;

a second element having first and second porous electrodes on opposite sides of an oxygen ion-conductive solid electrolyte plate;

means for defining a gas compartment disposed between said second electrode of the first element and said first element and said first electrode of the second element, said gas compartment defining means having a gas diffusion limiting portion through which said gas compartment communicates with the gaseous atmosphere;

means for defining an internal reference oxygen source in contact with said first electrode of the first element for collecting oxygen extracted at said first electrode of said first element from said gas compartment; and leakage resisting portion means for enabling gradual movement of oxygen from said internal reference oxygen source means to said gas compartment.

10. The air/fuel ratio sensor of claim 9, wherein each of said first and second porous electrodes of the first element contains a porous lead portion, and wherein said leakage resisting portion means comprises a porous insulator extending from one of said first and second porous electrodes of the first element, and a through-hole disposed between said porous insulator and said porous lead portion of the other of said first and second porous electrodes of the first element.

11. The air/fuel ratio sensor of claim 10, wherein said through hole is filled with a porous material.

12. The air/fuel ratio sensor of claim 11, wherein said porous material filling said through-hole is of the same material of which said porous electrodes of the first element are formed.

13. The air/fuel ratio sensor of claim 10, wherein said through-hole is unfilled.

14. The air/fuel ratio sensor of claim 9, wherein each of said first and second porous electrodes of said first element contains a porous lead portion, and wherein said leakage resisting portion means comprises a porous insulator extending from said porous lead portion of one of said first and second porous electrodes of said first element and substantially orthogonal thereto and connected to a terminal portion of the other one of said first and second porous electrodes, and a through-hole disposed between said terminal portion and said porous insulator.

15. The air/fuel ratio sensor of claim 14, wherein said through-hole is filled with a conductive porous material and serves to make external connection between said terminal portion and said porous insulator.

16. The air/fuel ratio sensor of claim 14, wherein said through-hole is lined with a conductive material and serves to make external electrical connection between said terminal portion and said porous insulator.

* * * * *